United States Patent [19]

Aretz et al.

[11] Patent Number: 5,527,697

[45] Date of Patent: Jun. 18, 1996

[54] 7-AMINO-3-METHOXYMETHYL-3-CEPHEM-4-CARBOXYLIC ESTER HYDROLASE, PROCESS FOR ITS PREPARATION, AND ITS USE

[75] Inventors: Werner Aretz, Königstein/Taunus; Klaus Sauber, Bad Soden am Taunus, both of Germany

[73] Assignee: Hoechst Aktiengesellschaft, Frankfurt am Main, Germany

[21] Appl. No.: 273,622

[22] Filed: Jul. 12, 1994

Related U.S. Application Data

[63] Continuation of Ser. No. 70,522, Jun. 3, 1993, abandoned.

[30] Foreign Application Priority Data

Jun. 6, 1992 [DE] Germany .................. 42 18 785.0

[51] Int. Cl.⁶ .................. C12N 9/18; C12P 35/00; C12P 41/00
[52] U.S. Cl. .................. 435/197; 435/47; 435/280; 435/872; 435/886
[58] Field of Search .................. 435/47, 280, 197, 435/872, 886

[56] References Cited

U.S. PATENT DOCUMENTS 4,316,955  2/1982  Abbott et al. .................. 435/47

FOREIGN PATENT DOCUMENTS

| 265185 | 4/1988 | European Pat. Off. . |
| 2215687C3 | 12/1980 | Germany . |
| 3344912C2 | 10/1989 | Germany . |

OTHER PUBLICATIONS

Shim Y K et al, Bull Korean Chem Soc. 10:33–34 (1989).
Jones J B, Tetrahedron 42:3351–3403 (1986).
"Deprotection of Carboxylic Esters of β–Lactam Homologues, Cleavage of p–Methoxybenzyl, Diphenylmethyl, and tert–Butyl Esters Effected by a Phenolic Matrix", Sigeru Torii et al., J. Org. Chem., 56:3633–3637 (1991).

*Primary Examiner*—Michael G. Wityshyn
*Assistant Examiner*—S. Saucier
*Attorney, Agent, or Firm*—Finnegan, Henderson, Farabow, Garrett & Dunner

[57] ABSTRACT

An esterase with a molecular weight of 55,200 ±300 Da is suitable for the chemoselective conversion of a compound of the formula II into a compound of the formula I.

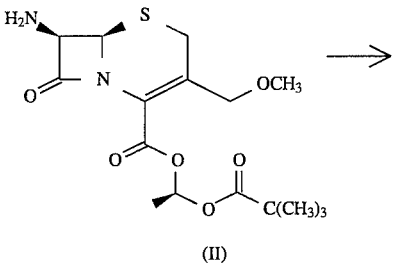

(II)

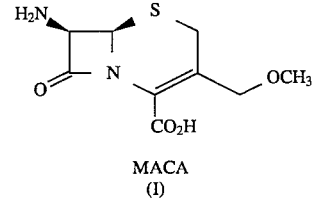

MACA
(I)

2 Claims, No Drawings

7-AMINO-3-METHOXYMETHYL-3-CEPHEM-4-CARBOXYLIC ESTER HYDROLASE, PROCESS FOR ITS PREPARATION, AND ITS USE

This application is a continuation of application Ser. No. 08/070,522, filed Jun. 3, 1993, now abandoned.

The synthesis of oral cephalosporins starting from 7-amino-3-methoxymethyl-3-cephem-4-carboxylic acid (MACA) (I), results in a mixture of (1R,S)-1-(2,2-dimethylpropionyloxy)-ethyl 7-amino-3-methoxymethyl-3-cephem-4-carboxylate isomers (pro-J-MACA ester or pro-K-MACA ester) (II).

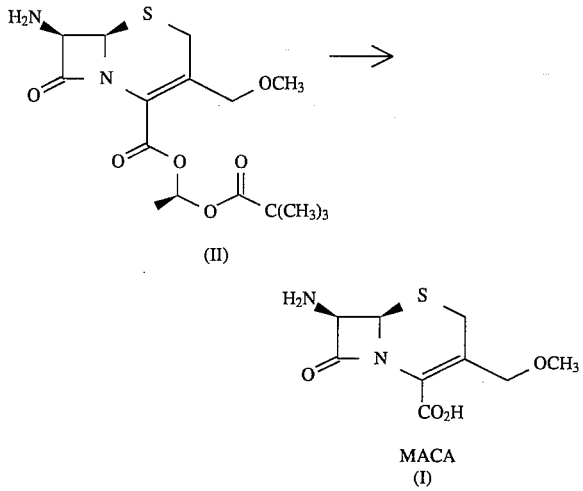

Following separation into R and S diastereomers, the unwanted R diastereomer, which still contains S constituent, must be reconverted into (I) by a non-stereoselective but chemoselective reaction.

The methods of ester cleavage known from the literature require reaction conditions which do not permit their use, in a satisfactory manner, for 7-amino-3-methoxymethyl-3-cephem-4-carboxylic esters, on account of the labile β-lactam ring. Thus, for example, the alkaline hydrolysis of esters with bases such as KOH, NaOH or sodium alcoholates in water or in organic solvents such as, for example, dioxane or alcohol simply leads to decomposition products. The cleavage of cephalosporin esters by means of phenol and acid catalysis has been described by S. Torii et al. (J. Org. Chem. 56 (1991) 3633). However, use of this method for 7-amino-3-methoxymethyl- 3-cephem-4-carboxylic esters only supplied the desired carboxylic acid in low yield and insufficient purity.

Porcine liver esterase, which is readily available, is not suitable for the said reaction either, since it leads exclusively to cleavage of the S diastereomer.

It has now been found, surprisingly, that a microbiologically-obtained esterase is suitable for effecting the above-described ester cleavage in a chemoselective manner and in good yields. The enzyme, called MACA-ester hydrolase for short, is formed, inter alia, by pseudomonads and actinomycetes, in particular of the genera Streptomyces and Amycolatopsis, and secreted into the culture broth.

Very particularly suitable strains are *Streptomyces bambergiensis* ATCC 13879, *Amycolatopsis orientalis* ATCC 14930 and *Nocardia sp.* ATCC 53492.

The process for preparing the said esterase, to which process the present invention also relates, comprises the following steps:

Cultivation of the microorganisms in question takes place under usual conditions. Preferably, raising and cultivation is effected on complex media with, for example, corn-steep, meat extract, peptone, casein, yeast extract, gelatin, tryptone, nitrate or ammonium as nitrogen sources and soluble starch, dextrin, sucrose, glucose or glycerol as carbon sources. As minerals, magnesium, iron, calcium, sodium and cobalt can, inter alia, be added.

Cultivation takes place preferably at room temperature or slightly above, in particular at about 28° C. The cultivation time is, for example, 48–60 hr. The isolation of the esterase, which may be necessary, takes place in a usual manner, for example by filtration or centrifugation, in which case the esterase is present in the supernatant, which can then be, for example, lyophilized or subjected to an ultrafiltration. Further purification steps may be indicated and, for example, contain a precipitation stage (for example with ammonium sulfate) and/or a further centrifugation. For using the esterase it can also be worthwhile to immobilize the latter on a suitable carrier.

Suitable for immobilizing purified, partially purified or crude cell extracts which contain the esterase, are, for example, carrier-bound immobilization procedures. For example, the esterase can be coupled to the polymeric carrier by a covalent bond via a lysine residue which is not essential for the catalysis. A further possibility is adsorption of the esterase onto a carrier and subsequent crosslinking with, for example, glutaraldehyde.

Examples of suitable enzyme carriers are polymeric, porous carriers such as celluloses, e.g. DEAE-celluloses or CM-celluloses, Sepharoses, such as, for example, BrCN-activated Sepharoses or divinylsulfone-activated Sepharoses, modified polyacrylamide gels with amino groups or hydroxyl groups or various organic copolymers of acrylamide, methacrylates or methacrylamide and maleic anhydride. Additionally, copolymers of glycidyl methacrylate, allyl glycidyl ether, methylenebismethylacrylamide and methacrylamide, such as, for example, ®Eupergit, can also be employed as enzyme carriers.

Further suitable enzyme carriers are crosslinked polymers based on polyvinyl esters and polyvinyl alcohols according to DE-A 33 44 912. The anchoring reaction of the esterase on the enzyme carrier takes place in a known manner, such as, for example, described in DE-A 2 215 687. A particularly suitable enzyme carrier is VA-Epoxy-Biosynth from Riedel de Haen.

An enzyme from *A. orientalis* has a molecular weight of 55,200 ±300 Da (sodium dodecyl sulfate polyacrylamide gel electrophoresis) and a specific activity of about 15 mU/mg in the culture filtrate. The pH optimum lies at 6.5 to 7.5.

At room temperature and pH 7.0, it shows a stability of several days, which is sufficient for technical purposes. Following partial purification, the enzyme can be bound without difficulty, for example to the enzyme carrier VA-Epoxy-Biosynth®. The activity is normally determined by conversion of MACA-ester to MACA. HPLC or TLC is then employed for the quantitative evaluation of the amount of MACA that is formed.

Methods for determining the enzymatic activity:

| | |
|---|---|
| TLC system: | HPTLC silica gel 60 $F_{254}$ 10*20 |
| | 1-butanol:glacial acetic acid:ethanol:$H_2O$ |
| | 50:20:15:15 |
| | ® Desaga Densitometer CD 50 |
| HPLC system: | HPLC analysis: |
| | Column: ® LiChrospher 100 RP 18.5 μm |

| Gradient: | Mob. phase: | A = 0.1% ammonium acetate + tetrabutylammonium hydrogen sulfate (10 mg/l) B = A + 80% acetonitrile | |
|---|---|---|---|
| | t (min) | flow (ml/min) | % B |
| | 0 | 1.0 | 4 |
| | 6 | " | 8 |
| | 10 | " | 70 |
| | 18 | " | 80 |
| | 20 | " | 4 |
| | 24 | " | 4 |

Sample vol.: 10 or 20 µl
Wavelength: 260 nm

The esterase according to the invention is suitable for cleaving different carboxylic acid esters. It is particularly suitable for cleaving esters of monocarboxylic acids or dicarboxylic acids having up to 6 carbon atoms, which may optionally be substituted by F, Cl or Br, of naturally occurring amino acids, or of 7-amino-3-methoxymethyl-3-cephem-4-carboxylic acid, with a monohydric, dihydric or trihydric alcohol having up to 6 carbon atoms, in which the carbon chain may also be interrupted by a —C(O)O— group, or with phenol, which may also be substituted by nitro.

The esterase is particularly suitable for cleaving p-nitrophenyl acetate, 1(R,S)-1-(2,2-dimethylpropionyloxy)-ethyl 7-amino-3-methoxymethyl-3-cephem-4-carboxylate, (2,2-dimethylpropionyloxy)-methyl 7-amino- 3-methoxymethyl-3-cephem-4-carboxylate, 1,1-bis(pivaloyloxy)-ethane, ethyl propionate, ethyl pivalate, triacetin, tributyrin, alanine ethyl ester and ethyl 2-chloropropionate. The process is very particularly suitable for cleaving 1(R,S)-1-(2,2-dimethyl-propionyloxy)-ethyl amino- 3-methoxymethyl-3-cephem-4-carboxylate, ethylpropionate, ethyl pivalate, alanine ethyl ester and ethyl 2-chloropropionate, in particular for cleaving 1(R,S)-1-(2,2-dimethylpropionyloxy)-ethyl 7-amino-3-methoxymethyl- 3-cephem-4-carboxylate.

The cleavage of the esters, explained in a representative manner for the conversion of the compound of the formula II to the compound of the formula I, takes place preferably under the following conditions. The compound of the formula II is treated with the esterase in aqueous solution, which is preferably buffered to the region of pH 6.8 (for example potassium phosphate buffer), preferably with the esterase in a suitably immobilized form. Preferably the reaction is allowed to proceed at 25°–35° C., in particular at about 30° C. After about 6–8 hr the reaction is as a rule 95% complete. The reaction solution is separated from the enzyme by known methods, for example filtration. The compound of the formula I is isolated, for example by lyophilization, and subsequently, where appropriate, further purified, for example by recrystallization.

The invention is illustrated in more detail below by means of examples and the content of the patent claims.

EXAMPLE 1

The examination of suitable hydrolase producers was carried out after growing preliminary and main cultures of the strains in Müller Hinton medium (Difco) at 28° C. and 240 rpm.

After 3 days the following hydrolase activities were found:

| Strain | | % MACA formation after 16 hour |
|---|---|---|
| Str. bambergiensis | ATCC 13879 | 6 |
| Amycolatopsis orientalis sub. lurida | ATCC 14930 | 18 |
| Amycolatopsis sp. | ATCC 53492 | 39 |

Example 2

Preliminary culture of Nocardia sp. ATCC 53492 is carried out in a medium of the following composition:

| | |
|---|---|
| glucose | 20 g/L |
| yeast extract | 24 g/L |
| soybean meal | 8 g/L |
| NaCl | 1 g/L |
| CaCO₃ | 4 g/L |
| pH 7.0 | |

500 ml/2000 ml Erlenmeyer flask; 28° C.; 240 rpm; 3 days
Main culture medium:

| | |
|---|---|
| sol. starch | 10 g/L |
| glucose | 10 g/L |
| glycerol | 10 g/L |
| peptone | 5 g/L |
| cornsteep liq. | 2.5 g/L |
| yeast extract | 2 g/L |
| NaCl | 1 g/L |
| pH 7.2 | |

9L of medium/12L fermenter; inoculum = 6%; 28° C.; 350 rpm; aeration rate: 0.5 vvm After 48–60 hours the maximum hydrolase activity of >90% MACA formation in 4 hr is reached.

EXAMPLE 3

3.5 l of culture solution from Example 2 are separated by centrifugation into culture supernatant and biomass. The enzyme is present in the supernatant. This solution is lyophilized. 85 g of solid are stirred into 500 ml of 50 mM potassium phosphate solution, pH=7.8, and subsequently centrifuged. The almost clear, dark-brown solution is subjected to an ammonium sulfate precipitation. Instead of lyophilization, the culture filtrate may also be concentrated to 500 ml by means of ultrafiltration (cut-off: 10,000 Da). Ammonium sulfate is then added to 35% saturation and the solution centrifuged once more. The supernatant is brought to 70% saturation with ammonium sulfate. After a further centrifugation at at least 13,000 g, the precipitate is taken up in 250 ml of buffer (see above). The activity of this solution is 370 mU/ml.

EXAMPLE 4

Sufficient primary and secondary phosphate is added to 250 ml of enzyme solution according to Example 3 to make the solution 1M with respect to phosphate. The pH is 8.0. A slight turbidity is acceptable. 50 g of the enzyme carrier VA-Epoxy Biosynth® (Riedel de Haen, Seelze, Germany) are then added and the mixture left to stand for 3 days at room temperature. Washing is then carried out with 1M NaCl and with double-distilled water. 72% of the enzyme activity is present on the carrier, which possesses a specific activity of 1.35 U/g dry weight.

EXAMPLE 5

2.5 g of R-ester hydrochloride are dissolved in 800 ml of 50 mM potassium phosphate solution, pH=6.8. 100 g of moist, immobilized enzyme are then added with stirring.

The pH is kept at 6.8 and the temperature at 30° C. Further 1.25 g amounts of substrate are added after 2.5 h and after 4¼ h. In all, the mixture contains 5 g of MACA ester (R). The cleavage proceeds within the space of 6–8 hours to 95% conversion according to HPLC. The cleavage solution is separated from the enzyme and lyophilized. About 10 g of a white solid are obtained.

EXAMPLE 6

The solid obtained from Example 5 is taken up in 35 ml of water, brought to pH=6.8 (dil. ammonia) and an insoluble residue is separated off. The clear, yellowish solution is then cooled down to 10° and 5N HCl is added with stirring. From pH=5.5 the MACA begins to crystallize out. The pH is further reduced to 2.5 and stirring continued for 20 minutes. The crystals are separated on a Seitz filter. They are then washed with water and acetone and finally with diisopropyl ether. The solid is dried in vacuo at room temperature. Weight: 2.2 g (96% purity) corresponding to 71% yield, based on the amount of MACA ester employed. 0.34 g of MACA, corresponding to 11.4%, remains in the mother liquor.

The following table contains further information concerning the substrate specificity of the esterase according to the invention:

| Substrate | Concentration | Activity U/ml | Activity U/mg | % |
|---|---|---|---|---|
| p-Nitrophenyl acetate (HEPES, pH 6.95) | 1.59 mM | 30.4 | 76.0 | 86.4 |
| p-Nitrophenyl acetate (phosphate buffer, pH 6.8) | 2.5 mM | 43.5 | 108.75 | 123.6 |
| MACA ester pro J | 2.5 mM | 35.2 | 87.75 | 100 |
| MACA ester pro K | 2.5 mM | 35.1 | 87.75 | 99.7 |
| 1,3-Bis(pivaloyloxy)-ethane | 50 mM | 1.4 | 3.5 | 4 |
| Ethyl propionate | 100 mM | 20 | 50 | 56.8 |
| Ethyl pivalate | 100 mM | 17.1 | 42.75 | 48.6 |

-continued

| Substrate | Concentration | Activity U/ml | Activity U/mg | % |
|---|---|---|---|---|
| Triacetin | 100 mM | 37.1 | 92.75 | 105.4 |
| Tributyrin | 100 mM | 37.5 | 93.75 | 106.5 |
| D,L-alanine ethyl ester | 100 mM | 16 | 40 | 45.5 |
| Ethyl 2-chloropropionate | 100 mM | 30 | 75 | 85.2 |

We claim:

1. An esterase which can bring about the chemoselective conversion of the compound of the formula II into the compound of the formula I

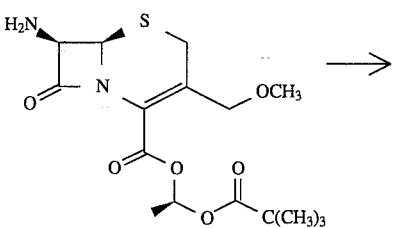

(II)

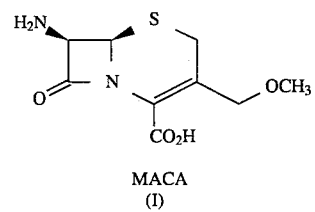

MACA
(I)

wherein said esterase can be prepared by cultivation of a microorganism selected from the group consisting of *Streptomyces bambergiensis, Amycolatopsis orientalis sub. lurida* and *Nocardia sp.* ATCC 53492.

2. The esterase as claimed in claim 1, which has a molecular weight of about 55,200 ±300 Da.

* * * * *